US008762171B2

(12) United States Patent
Knapp

(10) Patent No.: US 8,762,171 B2
(45) Date of Patent: Jun. 24, 2014

(54) MEDICAL RESOURCE ESTIMATION AND SIMULATION SYSTEM

(75) Inventor: Robert Ernest Knapp, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2324 days.

(21) Appl. No.: 11/356,673

(22) Filed: Feb. 17, 2006

(65) Prior Publication Data

US 2007/0055543 A1 Mar. 8, 2007

Related U.S. Application Data

(60) Provisional application No. 60/653,802, filed on Feb. 17, 2005.

(51) Int. Cl.
*G06Q 10/00* (2012.01)
(52) U.S. Cl.
USPC .................................................. 705/3; 705/2
(58) Field of Classification Search
USPC ........................................................ 705/2–3
See application file for complete search history.

(56) References Cited

U.S. PATENT DOCUMENTS

| 5,778,345 | A | 7/1998 | McCartney |
| 6,978,244 | B2 | 12/2005 | Rovinelli et al. |
| 2003/0140044 | A1* | 7/2003 | Mok et al. ........................ 707/10 |
| 2005/0038669 | A1 | 2/2005 | Sachdeva et al. |
| 2005/0075904 | A1* | 4/2005 | Wager et al. ...................... 705/2 |

* cited by examiner

*Primary Examiner* — Tran Nguyen
*Assistant Examiner* — Rajiv Raj
(74) *Attorney, Agent, or Firm* — Joshua B Ryan

(57) ABSTRACT

A healthcare decision support system simulates effects of a change in a number of patients. A repository includes patient specific clinical and non-clinical data, comprising multiple medical record attributes of multiple patients. A simulation processor receives data representing multiple factors for adjusting a value representing number of patients in corresponding multiple associated subsets of the multiple patients. An individual subset comprises patients having a particular medical record attribute of a particular type. A calculation processor identifies patients common to different particular subsets, and calculates a change in a value representing number of patients common to the different particular subsets by calculating a product of factors associated with the different particular subsets.

19 Claims, 4 Drawing Sheets

300
Simulation Applied to a Visit Cluster

400
Simulation Applying Multiple Simulation Rules
to a Historical Sample of Patient Visits

MEDICAL RESOURCE ESTIMATION AND SIMULATION SYSTEM

CROSS-REFERENCE TO RELATED APPLICATIONS

The present application is a non-provisional application of provisional application having Ser. No. 60/653,802 filed by Robert Ernest-Knapp on Feb. 17, 2005.

FIELD OF THE INVENTION

The present invention generally relates to computer information systems. More particularly, the present invention relates to a medical resource estimation and simulation system.

BACKGROUND OF THE INVENTION

Computer information systems ("systems") include computers that communicate with each other over a network, such as the Internet, and computers that manage information. For example, a healthcare enterprise uses systems to store and manage clinical and non-clinical information for patients in their care.

Healthcare enterprises employ simulation techniques to estimate, plan, or forecast the impact that changes to past operations will have on resources to service patients in the future. Factors that may be influenced or anticipated for a simulation include, for example: healthcare plans of employers, anticipated or planned changes in the medical staff, negotiations with third party payers, outreach facilities and changes in referral patterns, changes in the product line or delivery mode offered by the hospital, such as new, expanded, or discontinued services, patient population changes, and legislation and regulations.

When expectations for change can be captured by a single factor the task of quantifying expectations is straightforward. However, when multiple factors are involved, the problem is more complex and not satisfied by present solutions.

Prior case-mix simulation systems limit a simulation to a single factor such as diagnosis related groups (DRG) or doctor.

Prior simulation approaches that incorporate multiple factors include the following.

1. Set up a combined variable and treat it as a single variable. For example, create the combination "zip code—DRG," wherein "19312-142," for example, refers to patients living in zip code 19312 with DRG 142.

2. Use an algorithm that uses a tree-structured logic routine to create a single new dimension from multiple factors related to patients of a healthcare organization. The single new dimension is an indicator of case type or, in the aggregate, case mix. In this way, multiple dimensions are reduced to one dimension.

3. Use a tree-structure template as a model such as Doctors within DRGs. In this approach, rules may be defined at the DRG level, but, on an exception basis, go down to the Doctor level within selected DRGs.

4. Provide a combination of detailed rules and general rules for which the detailed rules would pre-empt the more general rule.

The first, third, and fourth approaches are limited in their flexibility, clumsy in their implementation, cumbersome to use, and unmanageable beyond two or three drivers. The second approach is flexible, but has other limitations described below.

The first approach creates too many combinations, each of which needs to be addressed separately. For example, suppose a patient population in zip code 19312 is going up by 20%, and in zip code 19301 is going down by 10%, while the obstetrics practices are being discontinued. A simulation for such an expectation requires entry of an expected percentage change for each combination of zip code and DRG in a database.

The second approach is similar to the first in that it reduces multiple dimensions to a single dimension. Although, the second approach is more sophisticated than the other approaches, it has a number of shortcomings. It is highly complex and its implementation requires software code to be written. Once the classification scheme for the approach has been settled and coded, it is rigidly applied. Because of this rigidity, the approach is often used by government agencies with the intent of classifying patients across multiple facilities (e.g., Medicare). The approach does not lend itself to settings in which the simulation scenarios can differ in the factors that are considered relevant, and in which the relevant factors are likely to change over time. The factors used in the tree-structured logic routine need to be generic factors, such as diagnosis codes, age, gender, etc., and do not incorporate factors such as zip code, physicians, and payer mix, which are needed when case mix simulation are utilized for budgeting and planning.

The third approach is more efficient that the first, but it forces the imposition of a tree structure of factors at the outset that does not reflect the underlying reality of the changes. Beyond two factors the third approach becomes increasingly restrictive and even the previous example in the first approach does not fit well into the third approach.

The fourth approach involves either an implicit or explicit hierarchy, and could not effectively be applied to the examples like the DRG and zip code.

The prior approaches increase processing burdens, increase computing resources, and reduce computational speed of simulation. Accordingly, there is a need for a medical resource estimation and simulation system that overcomes these and other disadvantages of the prior systems.

SUMMARY OF THE INVENTION

A healthcare decision support system simulates effects of a change in a number of patients. A repository includes patient specific clinical and non-clinical data, comprising multiple medical record attributes of multiple patients. A simulation processor receives data representing multiple factors for adjusting a value representing number of patients in corresponding multiple associated subsets of the multiple patients. An individual subset comprises patients having a particular medical record attribute of a particular type. A calculation processor identifies patients common to different particular subsets, and calculates a change in a value representing number of patients common to the different particular subsets by calculating a product of factors associated with the different particular subsets.

Table 1 illustrates simulation rules employing data representing a change in patient data for corresponding subsets of patient information, in accordance with invention principles.

Table 2 illustrates a first simulation including a first set of simulation rules, as shown in Table 1, for corresponding subsets of patient information, in accordance with invention principles.

Table 3 illustrates a second simulation including a second set of simulation rules, as shown in Table 1, for corresponding subsets of patient information, in accordance with invention principles.

Table 4 illustrates a third simulation including a third set of simulation rules, as shown in Table 1, for corresponding subsets of patient information, in accordance with invention principles.

Table 5 illustrates a fourth simulation including a fourth set of simulation rules, as shown in Table 1, for corresponding subsets of patient information, in accordance with invention principles.

Table 6 illustrates patient specific clinical and non-clinical information including subsets of patient information, in accordance with invention principles.

Table 7 illustrates application of the first simulation, as shown in Table 2, to the subsets of patient information, as shown in Table 6, in accordance with invention principles.

Table 8 illustrates application of the second simulation, as shown in Table 3, to the subsets of patient information, as shown in Table 6, in accordance with invention principles.

Table 9 illustrates application of the third simulation, as shown in Table 4, to the subsets of patient information, as shown in Table 6, in accordance with invention principles.

Table 10 illustrates application of the fourth simulation, as shown in Table 5, to the subsets of patient information, as shown in Table 6, in accordance with invention principles.

Table 11 illustrates a calculation involving a product of adjustment factors, corresponding to Tables 7-10, associated with different particular individual subsets of patient information, in accordance with invention principles.

Table 12 illustrates applying the product of adjustment factors to the different particular individual subsets of patient information to generate forecast patient information, in accordance with invention principles.

DETAILED DESCRIPTION OF THE PREFERRED EMBODIMENTS

Figure 1:
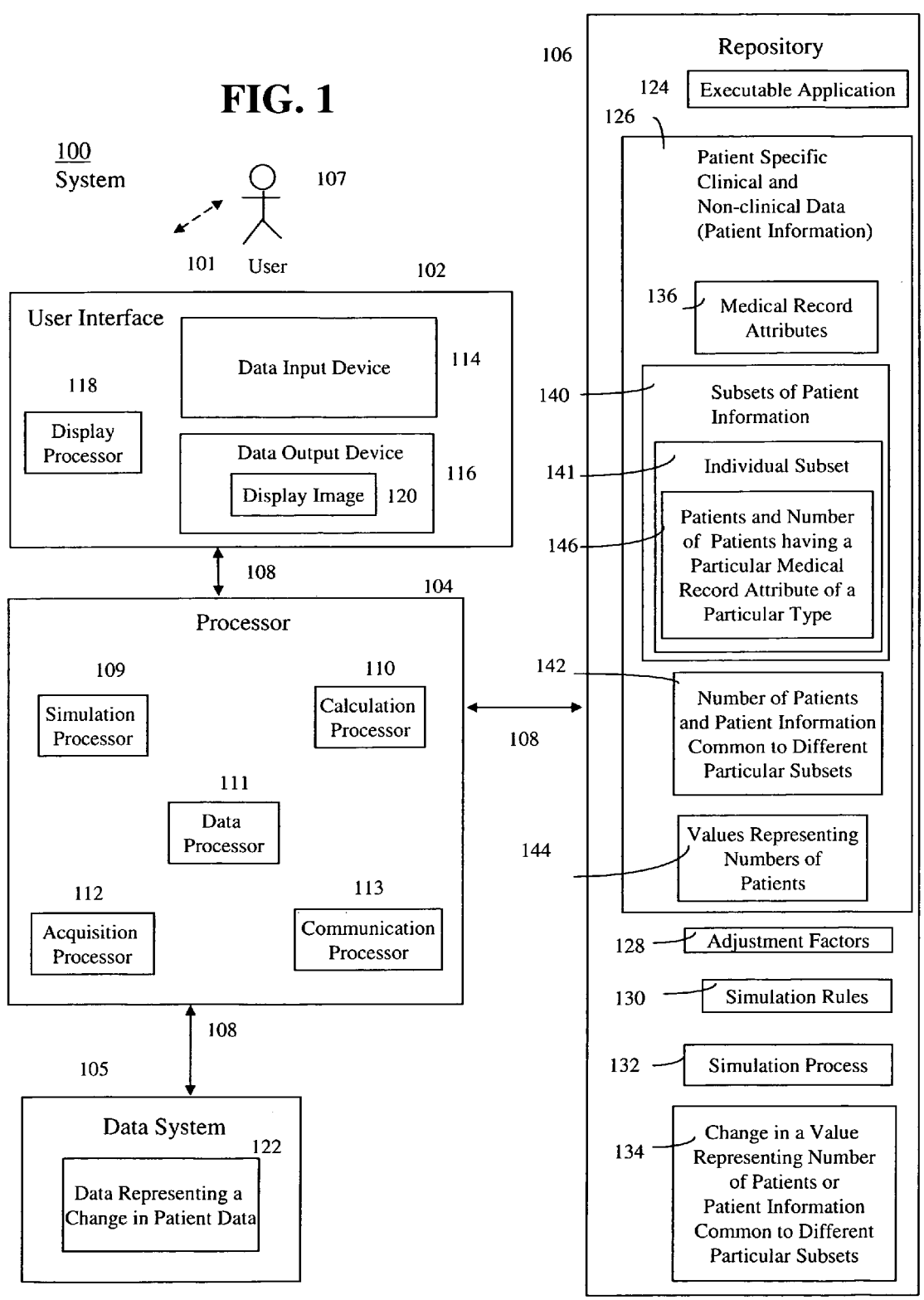
FIG. 1 illustrates a medical resource estimation and simulation system, in accordance with invention principles.

FIG. 1 illustrates a medical resource estimation and simulation system ("system") 100. The system 100 includes a user interface 102, a processor 104, and a repository 106. A user 107 and a data system 105 interact with the system 100.

A communication path 108 interconnects elements of the system 100, and/or interconnects the system 100 with the data system 105. The dotted line, near reference number 101, represents interaction between the user 107 and the user interface 102.

The user interface 102 further provides a data input device 114, a data output device 116, and a display processor 118. The data output device 116 further provides one or more display images 120, which are presented for viewing by the user 107.

The processor 104 further includes a simulation processor 109, a calculation processor 110, a data processor 111, an acquisition processor 112, and a communication processor 113.

The data system 105 further includes data representing a change in patient data 122. The data 122 embodies specific expectations of how the patient population of a future period might differ from a historical sample population. For example, the data 122 may represent a change in a number of patient visits.

The repository 106 further includes an executable application 124, patient specific clinical and non-clinical data 126 (otherwise called patient information), adjustment factors 128, simulation rules 130, a simulation process 132, and a change in value 134 representing number of patients or patient information common to different particular subsets of patient information. The patient specific clinical and non-clinical data 126 further includes medical record attributes 136, subsets of patient information 140, number of patients and patient information common to different particular subsets of patient information 142, and values representing numbers of patients 144. The subsets of patient information 140 further include individual subsets of patient information 141. The individual subset of patient information 141 further includes patients and number of patients having a particular medical record attribute of a particular type 146.

The data system 105 represents a source and/or a destination of any data 122 or other information that may be needed or used by the system 100 including, for example, any of the information stored in the repository 106. The data 122 may be pushed to the system 100 and/or pulled by the system 100, automatically and/or manually, at one time, periodically, or as needed. The data 122 may have any format and may represent any type of information.

The system 100 may be employed by any type of enterprise, organization, or department, such as, for example, providers of healthcare products and/or services responsible for servicing the health and/or welfare of people in its care. For example, the system 100 represents a healthcare information system. A healthcare provider provides services directed to the mental, emotional, or physical well being of a patient. Examples of healthcare providers include a hospital, a nursing home, an assisted living care arrangement, a home health care arrangement, a hospice arrangement, a critical care arrangement, a health care clinic, a physical therapy clinic, a chiropractic clinic, a medical supplier, a pharmacy, a doctor's office, and a dental office. When servicing a person in its care, a healthcare provider diagnoses a condition or disease, and recommends a course of treatment to cure the condition, if such treatment exists, or provides preventative healthcare services. Examples of the people being serviced by a healthcare provider include a patient, a resident, a client, and an individual.

The system 100 and/or elements contained therein also may be implemented in a centralized or decentralized configuration. The system 100 may be implemented as a client-server, web-based, or stand-alone configuration. In the case of the client-server or web-based configurations, the executable application 124 may be accessed remotely over a communication network, represented by communication path 108.

The communication path 108 (otherwise called network, bus, link, connection, channel, etc.) represents any type of protocol or data format. The protocol or data format includes, but is not limited to, one or more of the following: an Internet Protocol (IP), a Transmission Control Protocol Internet protocol (TCPIP), a Hyper Text Transmission Protocol (HTTP), an RS232 protocol, an Ethernet protocol, a Medical Interface Bus (MIB) compatible protocol, a Local Area Network (LAN) protocol, a Wide Area Network (WAN) protocol, a Campus Area Network (CAN) protocol, a Metropolitan Area Network (MAN) protocol, a Home Area Network (HAN) protocol, an Institute Of Electrical And Electronic Engineers (IEEE) bus compatible protocol, a Digital and Imaging Communications (DICOM) protocol, and a Health Level Seven (HL7) protocol.

The user interface 102 permits bi-directional exchange of data between the system 100 and the user 107 of the system 100 or another electronic device, such as a computer or an application, for example.

The data input device 114 typically provides data to a processor in response to receiving input data either manually from a user or automatically from another electronic device. For manual input, the data input device is a keyboard and a mouse, but also may be a touch screen, or a microphone and a voice recognition application, for example.

The data output device 116 typically provides data from a processor for use by a user or another electronic device. For output to a user, the data output device 116 is a display, such as, a computer monitor or screen, that generates one or more display images 120 in response to receiving the display signals from the display processor 118, but also may be a speaker or a printer, for example. The display images 120 provide information in any format including information used by a healthcare enterprise, such as any information/data stored in the repository 106. Examples of display images 120 include, for example, text, graphics, photos, images, graphs, charts, forms, tables, etc. Examples of display images 120 forming tables are shown in Tables 1-12.

The display processor 118 (e.g., a display generator) includes electronic circuitry or software or a combination of both for generating the display images 120 or portions thereof in response to receiving data representing display images, which may be stored in the repository 106. The data output device 116, implemented as a display, is coupled to the display processor 118 and displays the generated display images 120. The display images 120 provide, for example, a graphical user interface, permitting user interaction with the processor 104 or other device. The display processor 118 may be implemented in the user interface 102 and/or the processor 104.

The system 100, elements, and/or processes contained therein may be implemented in hardware, software, or a combination of both, and may include one or more processors, such as processor 104. Any appropriate allocation of processing functions among the disclosed processors may be employed. A processor is a device and/or set of machine-readable instructions for performing task. The processor includes any combination of hardware, firmware, and/or software. The processor acts upon stored and/or received information by computing, manipulating, analyzing, modifying, converting, or transmitting information for use by an executable application or procedure or an information device, and/or by routing the information to an output device. For example, the processor may use or include the capabilities of a controller or microprocessor.

The acquisition processor 112 acquires data 122, representing a change in patient data from the data system 105, or any other data used by the system 100. The acquisition processor 112 may acquire the data 122 directly or through the communication processor 113. The processor 104 (e.g., data processor 116 in processor 104) stores the data 122, which was acquired, as acquired data in the repository 106.

As an alternative to the acquisition processor 112, the processor 104 may acquire data 122 or any other data used by the system 100 via the user interface 102. For example, the user 107 may manually enter data into the data input device 114 (e.g., a keyboard) for use by the processor 104, or the data input device 114 (e.g., a data reader adapted to read a disc) may automatically enter data for use by the processor 104. In some cases, an automated function of the data input device 114 might provide the same or similar function as an automated function of the data system 105.

The communication processor 113 manages communications within the system 100 and outside the system 100, such as, for example, with the data system 105.

The simulation processor 109 and the calculation processor 110 together provide processing employed by the system 100, and are described in detail with reference to the remaining description. Generally, the simulation processor 109 receives appropriate data needed for processing by the calculation processor 110, according to the simulation rules 130 and the simulation process 132. The simulation processor 109 may receive the appropriate data from the user interface 102 (e.g., in response to user data entry), from the data system 105, and/or from the repository 106.

The data processor 111 performs general data processing for the system 100.

The repository 106 represents any type of storage device, such as computer memory devices or other tangible storage medium, for example. The repository 106 may be implemented as one or more distributed databases, for example.

An executable application, such as the executable application 124, comprises machine code or machine readable instruction for implementing predetermined functions including, for example, those of an operating system, a software application program, a healthcare information system, or other information processing system, for example, in response user command or input.

An executable procedure is a segment of code (i.e., machine readable instruction), sub-routine, or other distinct section of code or portion of an executable application for performing one or more particular processes, and may include performing operations on received input parameters (or in response to received input parameters) and providing resulting output parameters.

The patient specific clinical and non-clinical data 126 represent any information related to one or more patients. Particular information in the data 126 is represented by the medical record attributes 136, which may also be clinical or non-clinical.

Clinical data and attributes each represent information related to medical or health-related aspects of a patient's healthcare. Examples of clinical attributes include one or more of the following: (a) a diagnostic code, (b) a DRG (Diagnosis Related Group) code, (c) a treatment identifier, (d) a procedure identifier, (e) a medical condition identifier (f) healthcare provider visit type.

Non-clinical data and attributes each represent other various aspects related to supporting a patient's healthcare. Examples of non-clinical attributes include one or more of the following: (i) age, (ii) gender, (iii) weight, (iv) geographical area identifier, (v) healthcare provider, (vi) physician, (vii) medical insurance company, and (viii) number of healthcare provider visits.

The subsets of patient information 140 represent one or more individual subsets 141, including particular groups, or specific categories of patient information (i.e. patients) that have one or more medical record attributes (e.g., clinical and/or non-clinical) of a particular type 146 in common. For example, a subset of patient information 140 includes a list of patients, receiving care from a healthcare organization, that have a particular physician listed as their primary doctor. In another example, a subset of patient information 140 includes a list of patients, receiving care from a healthcare organization, residing in a particular geographic area. In yet another example, a subset of patient information 140 includes a list of patients, receiving care from a healthcare organization, that have a common diagnosis.

One or more individual subsets of patient information 140 may be combined to create patient information (e.g., clinical and/or non-clinical) that is common to one or more different subsets of patient information 142. For example, a combined subset of patient information 142 includes a list of patients, receiving care from a healthcare organization, that have a particular physician listed as their primary doctor, that live in a particular geographic area, and that have a common diagnosis.

The subsets of patient information 140, the individual subsets 141, and/or the patient information common to different particular subsets 142 may be determined by the user 107 in response to the processor (e.g., the simulation processor 109) receiving commands from the user interface 102.

The values, representing numbers of patients, 144 represent the number of patients in an individual subset of patient information 141. The values representing the numbers of patients 144 may be the actual numbers of patients, but are more likely to be a relative representation of the actual numbers of patients. For example, a value representing the numbers of patients 144 may be provided as 1.0, representing 100% of the patients in the individual subset of patient information 141, although the actual number of patients may be unknown or not relevant to a particular simulation or estimation.

The adjustment factors 128 are values, representing a change in a number of patients having a particular medical record attribute of a particular type 146, in an individual subset of patient information 141 and are based on the simulation rules 130. For example, an adjustment factor 128 having a value of 0.9 represents a change in a number of patients having a particular medical record attribute of a particular type 146 of minus 10%. In another example, an adjustment factor 128 having a value of 1.3 represents a change in a number of patients having a particular medical record attribute of a particular type 146 of plus 30%.

Figure 2:
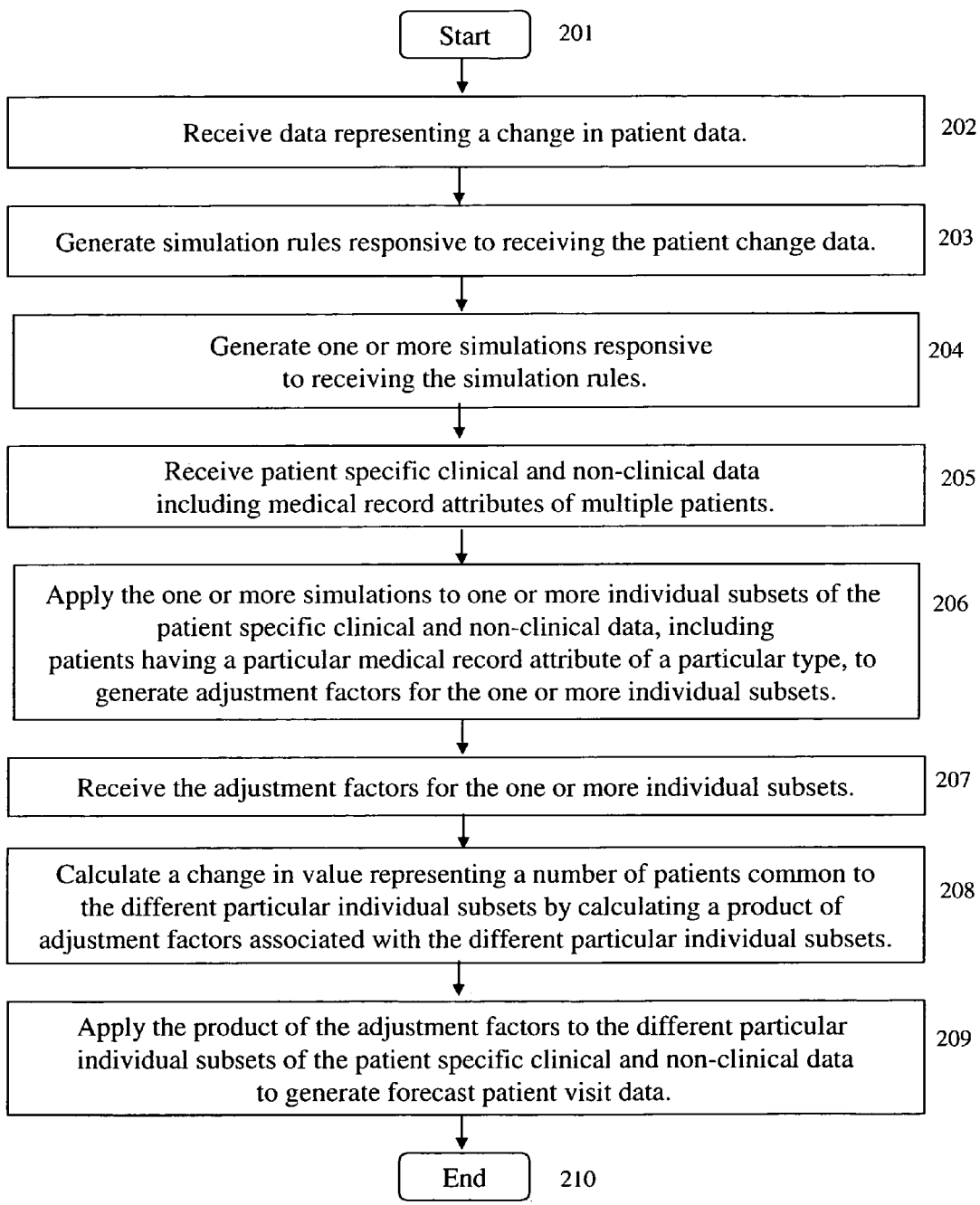
FIG. 2 illustrates a method for estimating and simulating medical resources for the system, as shown in FIG. 1, in accordance with invention principles.

The simulation rules 130 represent predefined decisions or choices for processing data, according to the method 200, as shown in FIG. 2. The simulation rules 130 may be created or modified manually by the user 107 (e.g., via the user interface 102), automatically by the processor 104, or by a combination of the user 107 and the processor 104.

A simulation process 132 represents a method, determination, or algorithm for processing data, according to the simulation rules 130. FIG. 2 illustrates an example of the simulation process 132, which is described as method 200.

The change in value 134, representing patient information common to different particular subsets of patient information, represents a product of adjustment factors 128 associated with different particular subsets of patient information. For example, a value 134 of 1.32 represents a product of adjustment factors 128 having values of 1.0, 1.2, 1.0, and 1.1 (i.e., 1.0×1.2×1.0×1.1). The change in value 134 quantifies the effect on other characteristics of the patient population and on aggregate measures, such as, for example, average length of stay, total cost, profitability, and volumes of detailed patient charges.

The system 100 employs the following principles, for example:

1. Reducing a multi-factor simulation to a set of single-factor simulations.
2. Using patient visit clusters to qualify each single-factor simulation to create the needed flexibility.
3. Determining a combined impact as being a product of the impacts of the single-factor simulations and the result of successive applications of single-factor simulations.

The system 100, for example, advantageously:

1. Provides a natural, modular way to simulate a potential change in patient mix involving multiple driving (i.e., change) factors.
2. Permits a user focus on a single driver at a time.
3. Provides a natural, reasonable, intuitive, easy to apply, flexible, and understandable way to model the combined impacts of one or more factors that may affect a patient population.
4. Provides a powerful method to capture highly complex simulation scenarios.
5. Reduces processing burdens, reduce computing resources, and increases computational speed of simulation.

The system 100, for example, provides a modular approach in which:

1. A factor can be re-used for other, related simulations for which other components might vary.
2. By setting up multiple combinations of single-factor simulations, multiple related alternative scenarios may be generated and compared. For example, a sensitivity analysis may be performed keeping one of the driving factors constant and varying the remaining factors.
3. Coding and maintaining the underlying algorithm are also facilitated by the system 100.

In the system 100, a single factor simulation provides a foundation for a multi-factor simulation. To define a single factor simulation, one selects a dimension (e.g., DRG) to serve as a driver, and then quantifies a percentage change for each value of the driving dimension that is expected to change (e.g. for each DRG). For example, it might be anticipated that the number of patients in DRG 14 is going to increase by 10%, and that the number of patients in DRG 15 is going to decrease by 5%. This means multiplying the number of patients in DRG 14 by 1.1 and multiplying the number of patients in DRG 15 by 0.95. Other DRGs would get a factor of 1, representing a 0% change.

A particular driver might apply to a subset of the patient population. For example, the DRG changes above might apply to patients at least 20 years old residing in zip code 19312. The number of patients not included in this subset would remain unchanged, at least as far as this driver is concerned.

The subset of patient visits specified as satisfying a set of rules (like patients 20+ years of age living in zip code 19312) is called a "Visit Cluster." A single-factor simulation is associated with a Visit Cluster that limits the applicability of the factor within the sample population. A multi-factor simulation is determined by a specifying a set of single-factor simulations, including their associated Visit Clusters. The impact of a multi-factor simulation is the product of its component single-factor simulations.

The system 100, for example, models a multi-factor simulation as:

1. A set of single-factor simulations.
2. Applied to respective Visit Clusters.
3. With a multi-factor impact implemented as a product of the single factor impacts.

The impact of either a single-factor or a multi-factor simulation involves measures that can be expected to vary directly with the number of patients of a particular type. Examples would include total patient days, total patient count, total number of services of a particular type, a count of patients receiving MRIs, a count of diabetic patients, total charges, and total variable cost.

Considering patient costs, the joint impact of the component single-factor simulations may be derived by applying them successively, wherein each single-factor simulation is applied to a result of the previous single-factor simulation. The rule for costs would be: leave the fixed costs unchanged and apply the factors to the variable costs. In this example, it would not matter and would not affect the final outcome in which order these single-factor simulations were applied. If order was of consequence, an order for applying the single-factor simulations is specified.

FIG. 2 illustrates a method 200 for estimating and simulating medical resources for the system 100, as shown in FIG. 1. Tables 1-12 below describe a particular example of the method 200. The example illustrates a way that a user determines a multi-factor simulation and how the system 100 applies rules to determine the impact of the simulation.

At step 201, the method 200 starts.

At step 202, the acquisition processor 112 receives data 122, representing a change in patient data, from the data system 105. An example of the data 122 includes the following information, represented as rules:

1. Other things being equal, the patients of Dr. Jones will decrease by 10%.
2. The patients of Dr. Smith in DRG 5 will increase by 20%, and in DRG 10 will decrease by 20%.
3. For other Doctors in the healthcare organization, the patients in DRG 391 will drop to zero, the patients in DRG 14 will increase by 50%, and the patients in DRG 10 will increase by 40%.
4. After giving effect to other information, the patients of Dr. Johnson will increase by 30%. 5. While the population in zip code 19312 is holding steady, the population in zip code 19301 is expected to increase by 10 percent.

At step 203, the simulation processor 109 generates simulation rules 130 responsive to receiving the patient change data 122. Table 1 illustrates simulation rules 130 employing the received data 122.

At step 204, the simulation processor 109 generates one or more simulations responsive to receiving the simulation rules 130. Tables 2, 3, 4, and 5 illustrate first, second, third, and fourth simulations, respectively, including a first, second, third, and fourth sets of simulation rules, respectively, as shown in Table 1, for corresponding subsets of patient information 140.

At step 205, the simulation processor 109 receives patient specific clinical and non-clinical data 126, including medical record attributes 136 of multiple patients, from the repository 106, and identifies patients common to different particular individual subsets 142, as shown in Table 6, for example.

At step 206, the simulation processor 109 applies the one or more simulations to one or more individual subsets 141 of the patient specific clinical and non-clinical data 126, including patients having a particular medical record attribute of a particular type 146, to generate adjustment factors 128 for the one or more individual subsets 141. For example, the simulation processor 109 applies simulations shown in Tables 2, 3, 4, and 5 to the individual subsets 141 of the patient specific clinical and non-clinical data 126, as shown in Table 6, to generate adjustment factors 128, as shown in Tables 7, 8, 9, and 10, respectively. Tables 7, 8, 9, and 10 provide first, second, third, and fourth set of adjustment factors 128, respectively, for corresponding individual subsets 141 of patient information. The simulation processor 109 stores the adjustment factors 128 in the repository 106.

At step 207, the simulation processor 109 receives the adjustment factors 128 for the one or more individual subsets 141 of patient information from the repository 106.

At step 208, the calculation processor 110 calculates a change in value representing a number of patients common to the different particular individual subsets 134 by calculating a product of adjustment factors 128 associated with the different particular individual subsets 141, as shown in Table 11.

At step 209, the calculation processor 110 applies the product of the adjustment factors to the different particular individual subsets 141 of the patient specific clinical and non-clinical data 126 to generate forecast patient visit data, as shown in Table 12.

At step 210, the method 200 ends.

Figure 3:
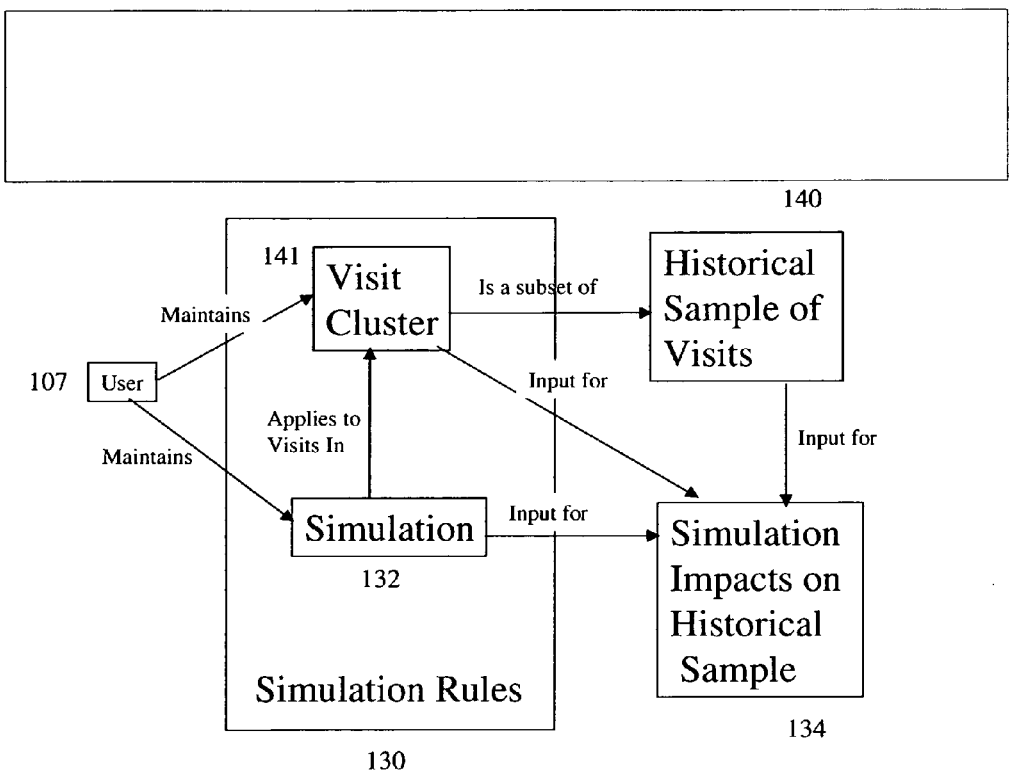
FIG. 3 illustrates a block diagram of a simulation applied to a subset of patient information, in accordance with invention principles.

FIG. 3 illustrates a block diagram of a simulation 300 applied to an individual subset of patient information 141, as exemplified in Table 12. The user 107 determines the desired individual subset of patient information 141 (i.e., the patient visit cluster) and the desired simulation process 132. The individual subset of patient information 141 is a subset of historical patient information 140 derived from the patient specific clinical and non-clinical data 126 (e.g., historical sample of patient visits). The simulation processor 109 applies the simulation process 132 to the individual subset of patient information 141, according to the simulation rules 130. The simulation processor 109 determines a change in value 134, representing patient information common to different particular subsets, to determine the impact of the simulation on the historical sample of patient visits in response to receiving the simulation process 132 (using the simulation rules 132), the patient visit cluster 141, and the historical sample of patient visits 140.

Figure 4:
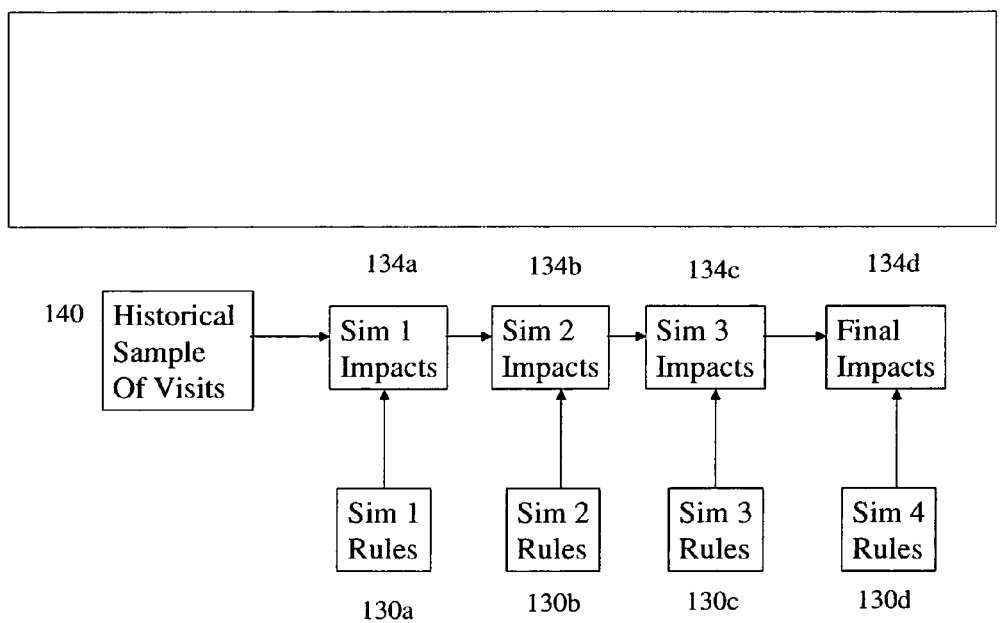
FIG. 4 illustrates a block diagram of a simulation applying multiple simulation rules to a historical subset of patient information, in accordance with invention principles.

FIG. 4 illustrates a block diagram of a simulation 400 applying multiple simulation rules 130 to historical individual subsets of patient information 141. The simulation processor 109 and the calculation processor 110 apply the first set of simulation rules 130a to the historical individual subsets of patient information 141 to generate a first impact or result of the simulation 134a. The simulation processor 109 and the calculation processor 110 apply the second set of simulation rules 130b to the first impact of the simulation 134a to generate a second impact of the simulation 134b. The simulation processor 109 and the calculation processor 110 apply the third set of simulation rules 130c to the second impact of the simulation 134b to generate a third impact of the simulation 134c. The simulation processor 109 and the calculation processor 110 apply the fourth set of simulation rules 130d to the third impact of the simulation 134c to generate a fourth impact of the simulation 134d. The simulation 400 advantageously permits the impacts of the simulation 134a-d, based on the various simulation rules, to be determined individually or collectively, in one or more steps.

The system 100 permits determination of a multi-factor simulation, and models its impact on a sample patient population of a healthcare organization to provide an estimated forecast. For example, the simulation processor 109 receives four factors 128, according to step 207 in FIG. 2, as shown in Table 11, for example. A first factor 128 adjusts a value representing a number of patients in a corresponding first subset of the multiple patients having a first medical record attribute (e.g., DRG) of a first type (e.g., DRG 1). A second factor 128 adjusts a value representing a number of patients in a corresponding second subset of the multiple patients having a first medical record attribute (e.g., DRG) of a different second type (e.g., DRG 5). A third factor 128 adjusts a value representing a number of patients in a corresponding third subset of the multiple patients having a second medical record attribute (e.g., Zip code) of a first type (e.g., Zip code 19301). A fourth factor 128 adjusts a value representing a number of patients in a corresponding fourth subset of the multiple patients having a second medical record attribute (e.g., Zip code) of a different second type (e.g., Zip code 19312).

The calculation processor 110 identifies patients common to different particular subsets, and calculates a change in a value, representing a number of patients common to the different particular subsets, 134 by calculating a product of factors 128 associated with the different particular subsets 141, as shown in Table 11.

In particular, the calculation processor 110 may identify patients common to two or more different particular subsets 142, and calculate a cumulative change in number of patients 134, common to the two or more different particular subsets 142, by calculating a product of factors 128 associated with the two different particular subsets.

Table 1 illustrates simulation rules 130 employing data 122, representing a change in patient data, for corresponding subsets of patient information 141. The columns in Table 1 include a single factor simulation number, a dimension (e.g., Doctor, DRG, and ZIP code), a subset of patient information 140 (also called a patient visit cluster), and comments. Simulation number one combines data 122, listed as rules 1 and 2, received in step 202 of method 200 (FIG. 2). Simulations 2, 3, and 4 implements data 122, listed as rules 2, 3, and 4, 10 received in step 202 of method 200 (FIG. 2). A user is permitted to select the four single-factor simulations to simulate the effect of the four simulations on a healthcare organization.

TABLE 1

| Single Factor Sim # | Dimension | Visit Cluster | Comments |
| --- | --- | --- | --- |
| 1 | Doctor | Patients of Dr. Jones and Dr. Johnson | This combines rules 1 and 4 |
| 2 | DRG | Patients of Dr. Smith with DRG 5 or 10 | Implements Rule 2 |
| 3 | DRG | Patients of every doctor except for Jones and Smith | Implements Rule 3 |
| 4 | Zip Code | Everybody in Sample Population | Implements Rule 5 |

Table 2 illustrates a first simulation including a first set of simulation rules (e.g., single factor simulation number one), as shown in Table 1, for corresponding subsets of patient information 140. Table 2 illustrates that the patients for Doctor Jones will decrease by 10%, and that the patients for Doctor Johnson will increase by 30%.

TABLE 2

| Doctor | Percentage Change |
| --- | --- |
| Jones | −10 |
| Johnson | 30 |

Table 3 illustrates a second simulation including a second set of simulation rules (e.g., single factor simulation number two), as shown in Table 1, for corresponding subsets of patient information 140. Table 3 illustrates that the patients for DRG 5 will increase by 20%, and that patients for DRG 10 will decrease by 20%.

TABLE 3

| DRG | Percentage Change |
| --- | --- |
| 5 | 20 |
| 10 | −20 |

Table 4 illustrates a third simulation including a third set of simulation rules (e.g., single factor simulation number three), as shown in Table 1, for corresponding subsets of patient information 140. Table 3 illustrates that the patients for DRG 10 will increase by 40%, that patients for DRG 14 will increase by 50%, and that patients for DRG 391 will decrease by 100% (i.e., to zero).

TABLE 4

| DRG | Percentage Change |
| --- | --- |
| 1 |  |
| 5 |  |
| 10 | 40 |
| 14 | 50 |
| 391 | −100 |

Table 5 illustrates a fourth simulation including a fourth set of simulation rules (e.g., single factor simulation number four), as shown in Table 1, for corresponding subsets of patient information 140. Table 5 illustrates that the patient population for ZIP code 19301 will increase by 10%, and that the patient population for ZIP code 19312 will remain the same (i.e., 0% change).

TABLE 5

| Zip Code | Percentage Change |
| --- | --- |
| 19301 | 10 |
| 19312 |  |

Table 6 illustrates patient specific clinical and non-clinical data 126 including subsets of patient information 140 (e.g. patient simulation population) common to different particular 20 individual subsets 142 of patient information. The columns in Table 6 include doctor, DRG, Zip code, a patient visit count and total charges for the corresponding patient. For example, patient "Smith" belongs to eight different particular individual subsets 142 of patient information, patient "Jones" belongs to ten different subsets 142, patient "Johnson" belongs to 8 different subsets 142, and patient "Peters" belongs to six different subsets 142.

TABLE 6

| Doctor | DRG | Zip Code | Visit Count | Total Charges |
| --- | --- | --- | --- | --- |
| Smith | 1 | 19301 | 2 | 20000 |
| Smith | 5 | 19301 | 3 | 30000 |
| Smith | 10 | 19301 | 4 | 40000 |
| Smith | 10 | 19312 | 10 | 4000 |
| Smith | 14 | 19301 | 5 | 50000 |
| Smith | 14 | 19312 | 20 | 60000 |
| Smith | 391 | 19301 | 6 | 40000 |
| Smith | 391 | 19312 | 30 | 4000 |

TABLE 6-continued

| Doctor | DRG | Zip Code | Visit Count | Total Charges |
|---|---|---|---|---|
| Jones | 2 | 19301 | 10 | 30000 |
| Jones | 5 | 19301 | 12 | 20000 |
| Jones | 10 | 19301 | 6 | 100000 |
| Jones | 10 | 19312 | 40 | 50000 |
| Jones | 14 | 19301 | 8 | 80000 |
| Jones | 14 | 19312 | 11 | 30000 |
| Jones | 25 | 19312 | 30 | 10000 |
| Jones | 31 | 19312 | 1 | 8000 |
| Jones | 391 | 19301 | 20 | 60000 |
| Jones | 391 | 19312 | 2 | 1000 |
| Johnson | 1 | 19312 | 4 | 9000 |
| Johnson | 5 | 19301 | 10 | 90000 |
| Johnson | 10 | 19301 | 20 | 20000 |
| Johnson | 10 | 19312 | 6 | 2000 |
| Johnson | 14 | 19301 | 4 | 50000 |
| Johnson | 14 | 19312 | 8 | 20000 |
| Johnson | 391 | 19301 | 2 | 25000 |
| Johnson | 391 | 19312 | 12 | 24000 |
| Peters | 5 | 19301 | 30 | 30000 |
| Peters | 5 | 19312 | 20 | 30000 |
| Peters | 10 | 19301 | 10 | 40000 |
| Peters | 10 | 19312 | 25 | 40000 |
| Peters | 14 | 19301 | 20 | 50000 |
| Peters | 391 | 19301 | 40 | 100000 |

Table 7 illustrates application of the first simulation, as shown in Table 2, to the subsets of patient information, as shown in Table 6, resulting in a first set of adjustment factors 128. The columns in Table 7 include doctor, DRG, Zip code, a determination the data is in a patient visit cluster, a percentage change in patient data, and an adjustment factor 128. For example, a 10% decrease in-patient visits results in an adjustment factor of 0.9, and a 30% increase in-patient visits results in an adjustment factor of 1.3.

TABLE 7

| Doctor | DRG | Zip Code | In Visit Cluster? | % Change | Factor |
|---|---|---|---|---|---|
| Smith | 1 | 19301 | | | 1 |
| Smith | 5 | 19301 | | | 1 |
| Smith | 10 | 19301 | | | 1 |
| Smith | 10 | 19312 | | | 1 |
| Smith | 14 | 19301 | | | 1 |
| Smith | 14 | 19312 | | | 1 |
| Smith | 391 | 19301 | | | 1 |
| Smith | 391 | 19312 | | | 1 |
| Jones | 2 | 19301 | Y | −10 | .9 |
| Jones | 5 | 19301 | Y | −10 | .9 |
| Jones | 10 | 19301 | Y | −10 | .9 |
| Jones | 10 | 19312 | Y | −10 | .9 |
| Jones | 14 | 19301 | Y | −10 | .9 |
| Jones | 14 | 19312 | Y | −10 | .9 |
| Jones | 25 | 19312 | Y | −10 | .9 |
| Jones | 31 | 19312 | Y | −10 | .9 |
| Jones | 391 | 19301 | Y | −10 | .9 |
| Jones | 391 | 19312 | Y | −10 | .9 |
| Johnson | 1 | 19312 | Y | 30 | 1.3 |
| Johnson | 5 | 19301 | Y | 30 | 1.3 |
| Johnson | 10 | 19301 | Y | 30 | 1.3 |
| Johnson | 10 | 19312 | Y | 30 | 1.3 |
| Johnson | 14 | 19301 | Y | 30 | 1.3 |
| Johnson | 14 | 19312 | Y | 30 | 1.3 |
| Johnson | 391 | 19301 | Y | 30 | 1.3 |
| Johnson | 391 | 19312 | Y | 30 | 1.3 |
| Peters | 5 | 19301 | | | 1 |
| Peters | 5 | 19312 | | | 1 |
| Peters | 10 | 19301 | | | 1 |
| Peters | 10 | 19312 | | | 1 |
| Peters | 14 | 19301 | | | 1 |
| Peters | 391 | 19301 | | | 1 |

Table 8 illustrates application of the second simulation, as shown in Table 3, to the subsets of patient information, as shown in Table 6, resulting in a second set of adjustment factors 128.

TABLE 8

| Doctor | DRG | Zip Code | In Visit Cluster? | % Change | Factor |
|---|---|---|---|---|---|
| Smith | 1 | 19301 | | | 1 |
| Smith | 5 | 19301 | Y | 20 | 1.2 |
| Smith | 10 | 19301 | Y | −20 | .8 |
| Smith | 10 | 19312 | Y | −20 | .8 |
| Smith | 14 | 19301 | | | 1 |
| Smith | 14 | 19312 | | | 1 |
| Smith | 391 | 19301 | | | 1 |
| Smith | 391 | 19312 | | | 1 |
| Jones | 2 | 19301 | | | 1 |
| Jones | 5 | 19301 | | | 1 |
| Jones | 10 | 19301 | | | 1 |
| Jones | 10 | 19312 | | | 1 |
| Jones | 14 | 19301 | | | 1 |
| Jones | 14 | 19312 | | | 1 |
| Jones | 25 | 19312 | | | 1 |
| Jones | 31 | 19312 | | | 1 |
| Jones | 391 | 19301 | | | 1 |
| Jones | 391 | 19312 | | | 1 |
| Johnson | 1 | 19312 | | | 1 |
| Johnson | 5 | 19301 | | | 1 |
| Johnson | 10 | 19301 | | | 1 |
| Johnson | 10 | 19312 | | | 1 |
| Johnson | 14 | 19301 | | | 1 |
| Johnson | 14 | 19312 | | | 1 |
| Johnson | 391 | 19301 | | | 1 |
| Johnson | 391 | 19312 | | | 1 |
| Peters | 5 | 19301 | | | 1 |
| Peters | 5 | 19312 | | | 1 |
| Peters | 10 | 19301 | | | 1 |
| Peters | 10 | 19312 | | | 1 |
| Peters | 14 | 19301 | | | 1 |
| Peters | 391 | 19301 | | | 1 |

Table 9 illustrates application of the third simulation, as shown in Table 4, to the subsets of patient information, as shown in Table 6, resulting in a third set of adjustment factors 128.

TABLE 9

| Doctor | DRG | Zip Code | In Visit Cluster? | % Change | Factor |
|---|---|---|---|---|---|
| Smith | 1 | 19301 | | | 1 |
| Smith | 5 | 19301 | | | 1 |
| Smith | 10 | 19301 | | | 1 |
| Smith | 10 | 19312 | | | 1 |
| Smith | 14 | 19301 | | | 1 |
| Smith | 14 | 19312 | | | 1 |
| Smith | 391 | 19301 | | | 1 |
| Smith | 391 | 19312 | | | 1 |
| Jones | 2 | 19301 | | | 1 |
| Jones | 5 | 19301 | | | 1 |
| Jones | 10 | 19301 | | | 1 |
| Jones | 10 | 19312 | | | 1 |
| Jones | 14 | 19301 | | | 1 |
| Jones | 14 | 19312 | | | 1 |
| Jones | 25 | 19312 | | | 1 |
| Jones | 31 | 19312 | | | 1 |
| Jones | 391 | 19301 | | | 1 |
| Jones | 391 | 19312 | | | 1 |
| Johnson | 1 | 19312 | Y | | 1 |
| Johnson | 5 | 19301 | Y | | 1 |
| Johnson | 10 | 19301 | Y | 40 | 1.4 |
| Johnson | 10 | 19312 | Y | 40 | 1.4 |
| Johnson | 14 | 19301 | Y | 50 | 1.5 |
| Johnson | 14 | 19312 | Y | 50 | 1.5 |
| Johnson | 391 | 19301 | Y | −100 | 0 |

TABLE 9-continued

| Doctor | DRG | Zip Code | In Visit Cluster? | % Change | Factor |
|---|---|---|---|---|---|
| Johnson | 391 | 19312 | Y | −100 | 0 |
| Peters | 5 | 19301 | Y | | 1 |
| Peters | 5 | 19312 | Y | | 1 |
| Peters | 10 | 19301 | Y | 40 | 1.4 |
| Peters | 10 | 19312 | Y | 40 | 1.4 |
| Peters | 14 | 19301 | Y | 50 | 1.5 |
| Peters | 391 | 19301 | Y | −100 | 0 |

Table 10 illustrates application of the fourth simulation, as shown in Table 5, to the subsets of patient information, as shown in Table 6, resulting in a fourth set of adjustment factors 128.

TABLE 10

| Doctor | DRG | Zip Code | In Visit Cluster? | % Change | Factor |
|---|---|---|---|---|---|
| Smith | 1 | 19301 | Y | 10 | 1.1 |
| Smith | 5 | 19301 | Y | 10 | 1.1 |
| Smith | 10 | 19301 | Y | 10 | 1.1 |
| Smith | 10 | 19312 | Y | | 1 |
| Smith | 14 | 19301 | Y | 10 | 1.1 |
| Smith | 14 | 19312 | Y | | 1 |
| Smith | 391 | 19301 | Y | 10 | 1.1 |
| Smith | 391 | 19312 | Y | | 1 |
| Jones | 2 | 19301 | Y | 10 | 1.1 |
| Jones | 5 | 19301 | Y | 10 | 1.1 |
| Jones | 10 | 19301 | Y | 10 | 1.1 |
| Jones | 10 | 19312 | Y | | 1 |
| Jones | 14 | 19301 | Y | 10 | 1.1 |
| Jones | 14 | 19312 | Y | | 1 |
| Jones | 25 | 19312 | Y | | 1 |
| Jones | 31 | 19312 | Y | | 1 |
| Jones | 391 | 19301 | Y | 10 | 1.1 |
| Jones | 391 | 19312 | Y | | 1 |
| Johnson | 1 | 19312 | Y | | 1 |
| Johnson | 5 | 19301 | Y | 10 | 1.1 |
| Johnson | 10 | 19301 | Y | 10 | 1.1 |
| Johnson | 10 | 19312 | Y | | 1 |
| Johnson | 14 | 19301 | Y | 10 | 1.1 |
| Johnson | 14 | 19312 | Y | | 1 |
| Johnson | 391 | 19301 | Y | 10 | 1.1 |
| Johnson | 391 | 19312 | Y | | 1 |
| Peters | 5 | 19301 | Y | 10 | 1.1 |
| Peters | 5 | 19312 | Y | | 1 |
| Peters | 10 | 19301 | Y | 10 | 1.1 |
| Peters | 10 | 19312 | Y | | 1 |
| Peters | 14 | 19301 | Y | 10 | 1.1 |
| Peters | 391 | 19301 | Y | 10 | 1.1 |

Table 11 illustrates a calculation a product of adjustment factors 128, corresponding to Tables 7-10, associated with different particular individual subsets 141 of patient information. The columns in Table 11 include doctor, DRG, Zip code, first, second, third, and fourth sets of adjustment factors 128 for the different individual subsets 141 of patient information, and the product of the adjustment factors 128. For example, in the $4^{th}$, $5^{th}$, $6^{th}$, and $7^{th}$ columns of Table 11, the $1^{st}$, $2^{nd}$, $3^{rd}$, and $4^{th}$ sets of adjustment factors 128, respectively, are copied from the sixth column of Tables 7, 8, 9, and 10, respectively. Column eight shows the product of the adjustment factors 128. For example, for individual subset 142, shown in the first row of Table 11 as "Smith, DRG-1, and Zip code—19301, the product of the four individual adjustment factors 128 is 1.1 (i.e., 1×1×1×1.1).

TABLE 11

| Doctor | DRG | Zip Code | Rule 1 Factor | Rule 2 Factor | Rule 3 Factor | Rule 4 Factor | Simulation Factor (Product for Rules 1-4) |
|---|---|---|---|---|---|---|---|
| Smith | 1 | 19301 | 1 | 1 | 1 | 1.1 | 1.1 |
| Smith | 5 | 19301 | 1 | 1.2 | 1 | 1.1 | 1.32 |
| Smith | 10 | 19301 | 1 | .8 | 1 | 1.1 | .88 |
| Smith | 10 | 19312 | 1 | .8 | 1 | 1 | .8 |
| Smith | 14 | 19301 | 1 | 1 | 1 | 1.1 | 1.1 |
| Smith | 14 | 19312 | 1 | 1 | 1 | 1 | 1 |
| Smith | 391 | 19301 | 1 | 1 | 1 | 1.1 | 1.1 |
| Smith | 391 | 19312 | 1 | 1 | 1 | 1 | 1 |
| Jones | 2 | 19301 | .9 | 1 | 1 | 1.1 | .99 |
| Jones | 5 | 19301 | .9 | 1 | 1 | 1.1 | .99 |
| Jones | 10 | 19301 | .9 | 1 | 1 | 1.1 | .99 |
| Jones | 10 | 19312 | .9 | 1 | 1 | 1 | .9 |
| Jones | 14 | 19301 | .9 | 1 | 1 | 1.1 | .99 |
| Jones | 14 | 19312 | .9 | 1 | 1 | 1 | .9 |
| Jones | 25 | 19312 | .9 | 1 | 1 | 1 | .9 |
| Jones | 31 | 19312 | .9 | 1 | 1 | 1 | .9 |
| Jones | 391 | 19301 | .9 | 1 | 1 | 1.1 | .99 |
| Jones | 391 | 19312 | .9 | 1 | 1 | 1 | .9 |
| Johnson | 1 | 19312 | 1.3 | 1 | 1 | 1 | 1.3 |
| Johnson | 5 | 19301 | 1.3 | 1 | 1 | 1.1 | 1.43 |
| Johnson | 10 | 19301 | 1.3 | 1 | 1.4 | 1.1 | 2.002 |
| Johnson | 10 | 19312 | 1.3 | 1 | 1.4 | 1 | 1.82 |
| Johnson | 14 | 19301 | 1.3 | 1 | 1.5 | 1.1 | 2.145 |
| Johnson | 14 | 19312 | 1.3 | 1 | 1.5 | 1 | 1.95 |
| Johnson | 391 | 19301 | 1.3 | 1 | 0 | 1.1 | 0 |
| Johnson | 391 | 19312 | 1.3 | 1 | 0 | 1 | 0 |
| Peters | 5 | 19301 | 1 | 1 | 1 | 1.1 | 1.1 |
| Peters | 5 | 19312 | 1 | 1 | 1 | 1 | 1 |
| Peters | 10 | 19301 | 1 | 1 | 1.4 | 1.1 | 1.54 |
| Peters | 10 | 19312 | 1 | 1 | 1.4 | 1 | 1.4 |
| Peters | 14 | 19301 | 1 | 1 | 1.5 | 1.1 | 1.65 |
| Peters | 391 | 19301 | 1 | 1 | 0 | 1.1 | 0 |

Table 12 illustrates applying the product of the adjustment factors 128 to the different particular individual subsets 142 of patient information to generate forecast patient information. The columns in Table 12 include doctor, DRG, Zip code, the product of the adjustment factors 128, the historical patient visit count, the historical total charges, the forecast patient visit count, and the forecast total charges. The product of the adjustment factors 128 is copied from the corresponding different particular individual subsets 142 of patient information in Table 11. The historical patient visit count and the historical total charges are each copied from the corresponding different particular individual subsets 142 of patient information in Table 6.

The calculation processor 110 determines a forecast patient visit count by multiplying the corresponding product of the adjustment factors 128 by the corresponding historical patient visit count for each of the different particular individual subsets 141 of patient information (e.g., in the first row of Table 12, 1.1×2=2.2).

The calculation processor 110 determines forecast patient total charges by multiplying the corresponding product of the adjustment factors 128 by the corresponding historical total charges for each of the different particular individual subsets 141 of patient information (e.g., in the first row of Table 12, 1.1×20000=22000).

The forecasted measures may be determined in various ways to find total impacts by Doctor, by DRG, or by Zip Code, for example. The calculations are performed, for example, at the patient level against a patient-level historical database. In this case, any dimension available in the sample database may be chosen as an "impact dimension" to determine the forecasted measures. For example, one may determine the impact on the number of patients and on total charges by hospital service. Further analysis of the result may compare these distributions by hospital service on a before-simulation and after-simulation basis.

TABLE 12

| Doctor | DRG | Zip Code | Simulation Factor | Historical Visit Count | Historical Total Charges | Forecast Visit Count | Forecast Total Charges |
|---|---|---|---|---|---|---|---|
| Smith | 1 | 19301 | 1.1 | 2 | 20000 | 2.2 | 22000 |
| Smith | 5 | 19301 | 1.32 | 3 | 30000 | 3.96 | 39600 |
| Smith | 10 | 19301 | .88 | 4 | 40000 | 3.52 | 35200 |
| Smith | 10 | 19312 | .8 | 10 | 4000 | 8 | 3200 |
| Smith | 14 | 19301 | 1.1 | 5 | 50000 | 5.5 | 55000 |
| Smith | 14 | 19312 | 1 | 20 | 60000 | 20 | 60000 |
| Smith | 391 | 19301 | 1.1 | 6 | 40000 | 6.6 | 44000 |
| Smith | 391 | 19312 | 1 | 30 | 4000 | 30 | 4000 |
| Jones | 2 | 19301 | .99 | 10 | 30000 | 9.9 | 29700 |
| Jones | 5 | 19301 | .99 | 12 | 20000 | 11.88 | 19800 |
| Jones | 10 | 19301 | .99 | 6 | 100000 | 5.94 | 99000 |
| Jones | 10 | 19312 | .9 | 40 | 50000 | 36 | 45000 |
| Jones | 14 | 19301 | .99 | 8 | 80000 | 7.92 | 79200 |
| Jones | 14 | 19312 | .9 | 11 | 30000 | 9.9 | 27000 |
| Jones | 25 | 19312 | .9 | 30 | 10000 | 27 | 9000 |
| Jones | 31 | 19312 | .9 | 1 | 8000 | .9 | 7200 |
| Jones | 391 | 19301 | .99 | 20 | 60000 | 19.8 | 59400 |
| Jones | 391 | 19312 | .9 | 2 | 1000 | 1.8 | 900 |
| Johnson | 1 | 19312 | 1.3 | 4 | 9000 | 5.2 | 11700 |
| Johnson | 5 | 19301 | 1.43 | 10 | 90000 | 14.3 | 128700 |
| Johnson | 10 | 19301 | 2.002 | 20 | 20000 | 40.04 | 40040 |
| Johnson | 10 | 19312 | 1.82 | 6 | 2000 | 10.92 | 3640 |
| Johnson | 14 | 19301 | 2.145 | 4 | 50000 | 8.58 | 100725 |
| Johnson | 14 | 19312 | 1.95 | 8 | 20000 | 15.6 | 38000 |
| Johnson | 391 | 19301 | 0 | 2 | 25000 | 0 | 0 |
| Johnson | 391 | 19312 | 0 | 12 | 24000 | 0 | 0 |
| Peters | 5 | 19301 | 1.1 | 30 | 30000 | 33 | 33000 |
| Peters | 5 | 19312 | 1 | 20 | 30000 | 20 | 30000 |
| Peters | 10 | 19301 | 1.54 | 10 | 40000 | 15.4 | 61600 |
| Peters | 10 | 19312 | 1.4 | 25 | 40000 | 35 | 56000 |
| Peters | 14 | 19301 | 1.65 | 20 | 50000 | 33 | 82500 |
| Peters | 391 | 19301 | 0 | 40 | 100000 | 0 | 0 |

Hence, while the present invention has been described with reference to various illustrative examples thereof, it is not intended that the present invention be limited to these specific examples. Those skilled in the art will recognize that variations, modifications, and combinations of the disclosed subject matter can be made, without departing from the spirit and scope of the present invention, as set forth in the appended claims.

What is claimed is:

1. A healthcare decision support system for simulating effects of a change in a number of patients, comprising:
at least one repository of information including patient specific clinical and non-clinical data comprising a plurality of medical record attributes of a plurality of patients;
a simulation processor for receiving data representing a plurality of numerical adjustment factors for adjusting a value representing number of patients identified in data in a corresponding plurality of associated subsets of said plurality of patients using information derived from said at least one repository, an individual subset comprising data identifying patients having a particular medical record attribute of a particular type; and
a calculation processor for identifying patients common to different particular subsets individually having a particular medical record attribute of a particular type and for calculating a change in a value representing number of patients common to said different particular subsets by calculating a product of numerical adjustment factors associated with said different particular subsets, said product representing a multi-factor simulation.

2. A system according to claim 1, wherein
said multi-factor simulation is derived from a plurality of single factor simulations,
the calculated product of numerical adjustment factors associated with said different particular subsets is used to estimate the effect a change on a number of patients in past healthcare operational data has on resources to service patients in the future,
said medical record attribute comprises a clinical or non-clinical attribute and a clinical attribute comprises at least one of, (a) a diagnostic code, (b) a DRG (Diagnosis Related Group) code, (c) a treatment identifier, (d) a procedure identifier, (e) a medical condition identifier (f) healthcare provider visit type and
said non-clinical attribute comprises at least one of, (i) age, (ii) gender, (iii) weight, (iv) geographical area identifier, (v) healthcare provider, (vi) physician, (vii) medical insurance company and (viii) number of healthcare provider visits.

3. A system according to claim 1, wherein
said corresponding plurality of associated subsets of said plurality of patients are within a set of said plurality of patients determined by said simulation processor in response to user command.

4. A system according to claim 1, wherein
said simulation processor receives said data in response to user data entry.

5. A healthcare decision support system for simulating effects of a change in a number of patients, comprising:
at least one repository of information including patient specific clinical and non-clinical data comprising a plurality of medical record attributes of a plurality of patients;
a simulation processor for using information derived from said at least one repository and for receiving data comprising,
a first numerical adjustment factor for adjusting a value representing a number of patients in a corresponding first subset of said plurality of patients having a first medical record attribute of a first type,
a second numerical adjustment factor for adjusting a value representing a number of patients in a corresponding second subset of said plurality of patients having a first medical record attribute of a different second type,
a third numerical adjustment factor for adjusting a value representing a number of patients in a corresponding third subset of said plurality of patients having a second medical record attribute of a first type and
a fourth numerical adjustment factor for adjusting a value representing a number of patients in a corresponding fourth subset of said plurality of patients having a second medical record attribute of a different second type; and
a calculation processor for identifying patients common to different particular subsets and for calculating a change in a value representing a number of patients common to said different particular subsets by calculating a product of numerical adjustment factors associated with said different particular subsets, said product representing a multi-factor simulation.

6. A system according to claim 5, wherein
said multi-factor simulation being derived from a plurality of single factor simulations and said calculation processor identifies patients common to two different particular subsets and calculates a cumulative change in number of patients common to said two different particular subsets by calculating a product of numerical adjustment factors associated with said two different particular subsets.

7. A method for simulating effects of a change in a number of patients, comprising the steps of:
employing at least one computer system for,
receiving patient specific clinical and non-clinical data, including medical record attributes of multiple patients;
applying one or more simulations to one or more individual subsets of the patient specific clinical and non-clinical data to generate corresponding numerical adjustment factors;
identifying patients common to different particular subsets;
calculating a change in value, representing a number of the identified patients common to the different particular individual subsets, by calculating a product of numerical adjustment factors associated with the different particular individual subsets; and
using the calculated product of numerical adjustment factors to estimate the effect of a change on a number of patients in past healthcare operational data on future data, said product representing a multi-factor simulation.

8. A method, according to claim 7, further comprising the steps of:
receiving data, representing a change in patient data;
generating simulation rules responsive to receiving the patient change data; and
generating the one or more simulations responsive to receiving the simulation rules.

9. A method, according to claim 7, further comprising the step of:
applying the product of the numerical adjustment factors to the different particular individual subsets of the patient specific clinical and non-clinical data to generate forecast patient data.

10. A method, according to claim 7, further comprising the step of:
selecting by a user the one or more simulations and the one or more individual subsets of the patient specific clinical and non-clinical data.

11. A method for simulating effects of a change in a number of patients, comprising the steps of:
employing at least one computer system for,
receiving data, representing a change in patient data;
generating simulation rules responsive to receiving the patient change data;
generating one or more simulations responsive to receiving the simulation rules;
receiving patient specific clinical and non-clinical data, including medical record attributes of multiple patients;
applying the one or more simulations to one or more individual subsets of the patient specific clinical and non-clinical data to generate corresponding numerical adjustment factors; and
calculating a change in value, representing a number of patients common to the different particular individual subsets individually having a particular medical record attribute of a particular type, by calculating a product of numerical adjustment factors associated with the different particular individual subsets; and
using the calculated product of numerical adjustment factors to estimate change in number of patients to service in the future, said product representing a multi-factor simulation.

12. A method, according to claim 11, further comprising the step of:
applying the product of the numerical adjustment factors to the different particular individual subsets of the patient specific clinical and non-clinical data to generate forecast patient data wherein
said multi-factor simulation is derived from a plurality of single factor simulations.

13. A method, according to claim 12, further comprising the step of:
selecting by a user the one or more simulations and the one or more individual subsets of the patient specific clinical and non-clinical data.

14. A method, according to claim 11, further comprising the step of:
selecting by a user the one or more simulations and the one or more individual subsets of the patient specific clinical and non-clinical data.

15. A user interface system permitting a user to simulate effects of a change in a number of patients, comprising:
at least one repository including patient specific clinical and non-clinical data comprising a plurality of medical record attributes of a plurality of patients;
a data input device permitting a user to select one or more simulations and one or more individual subsets of patient specific clinical and non-clinical data derived from said at least one repository, wherein the one or more simulations are applied to the one or more individual subsets of the patient specific clinical and non-clinical data to generate corresponding numerical adjustment factors; and
a data output device permitting a user to determine a change in value, representing a number of patients common to the different particular individual subsets by determining a product of numerical adjustment factors associated with the different particular individual subsets, said product representing a multi-factor simulation.

16. A user interface system, according to claim 15, wherein the data output device permits a user to determine forecast patient data by applying the product of the numerical adjustment factors to the different particular individual subsets of the patient specific clinical and non-clinical data and
said multi-factor simulation being derived from a plurality of single factor simulations.

17. A user interface system, according to claim 15, wherein the data input device is a keyboard, and herein the data output device is a display.

18. A method of using a user interface system by a user to permit the user to simulate effects of a change in a number of patients, comprising the steps of:
employing at least one computer system for,
receiving, from a user, one or more commands to select one or more simulations and one or more individual subsets of patient specific clinical and non-clinical data, wherein the one or more simulations are applied to the one or more individual subsets of the patient specific clinical and non-clinical data to generate corresponding numerical adjustment factors;
identifying patients common to different particular subsets;
determining, in response to user command, a change in value, representing a number of the identified patients common to the different particular individual subsets individually having a particular medical record attribute of a particular type by determining a product of numerical adjustment factors associated with the different particular individual subsets; and using the product of numerical adjustment factors to estimate change in number of patients to be handled in the future, said product representing a multi-factor simulation.

19. A method, according to claim 18, further comprising the step of:

determining, by the user, forecast patient data by applying the product of the numerical adjustment factors to the different particular individual subsets of the patient specific clinical and non-clinical data.

* * * * *